United States Patent
Scheffler

(10) Patent No.: US 7,650,178 B2
(45) Date of Patent: Jan. 19, 2010

(54) MAGNETIC FIELD SENSOR-BASED NAVIGATION SYSTEM TO TRACK MR IMAGE-GUIDED INTERVENTIONAL PROCEDURES

(75) Inventor: Klaus Scheffler, Basel (CH)

(73) Assignee: University of Basel, Basel (CH)

( * ) Notice: Subject to any disclaimer, the term of this patent is extended or adjusted under 35 U.S.C. 154(b) by 1004 days.

(21) Appl. No.: 10/835,544

(22) Filed: Apr. 30, 2004

(65) Prior Publication Data

US 2005/0245811 A1 Nov. 3, 2005

(51) Int. Cl.
*A61B 5/05* (2006.01)
(52) U.S. Cl. .................. 600/424; 600/410; 600/420; 324/207.13
(58) Field of Classification Search ............. 600/424, 600/410, 420; 324/207.13, 307
See application file for complete search history.

(56) References Cited

U.S. PATENT DOCUMENTS

| | | | |
|---|---|---|---|
| 5,307,808 A | 5/1994 | Dumoulin et al. | |
| 5,558,091 A * | 9/1996 | Acker et al. | 600/424 |
| 6,111,416 A | 8/2000 | Zhang et al. | |
| 6,427,314 B1 | 8/2002 | Acker | |
| 6,516,213 B1 | 2/2003 | Nevo | |

OTHER PUBLICATIONS

Bernstein, M.A. et al, "Concominant Gradient Terms in Phase Contrast MR: Analysis and Correction", Magn Reson Med 1998; 39:300-308.

Scheffler, K., "Basics of non-invasive angiography contrast-enhanced magnetic resonance angiography", JBR-BTR, Nov.-Dec. 2003;86(6):344-6.
Scheffler, K. et al, "Principles and applications of balanced SSFP techniques", Eur Radiol. Nov. 2003; 13(11); 2409-18.
Arnold, S.M. et al, "Dynamic contrast enhancement of paragangliomas of the head and neck: evaluation with time-resolved 2D MR projection angiography" Eur Radiol. Jul. 2003; 13(7); 1608-11.
Sonnet, S. et al, "Dynamic time-resolved contrast-enhanced two-dimensional MR projection angiography of the pulmonary circulation: standard technique and clinical applications", AJR AM J. Roentgenol. Jul. 2002; 179(1): 159-65.
Wetzel, S.G. et al, "Preliminary experience with dynamic MR projection angiography in the evaulation of cervicocranial steno-occulsive disease", Eur Radiol. 2001; 11(2):295-302.
Wetzel, S.G. et al, "Cerebral dural arteriovenous fistulas: detection by dynamic MR projection angiography", AJR Am J Roentgenol, May 2000; 174(5):1293-5.

(Continued)

*Primary Examiner*—Brian Casler
*Assistant Examiner*—John F Ramirez
(74) *Attorney, Agent, or Firm*—Griffin & Szipl, P.C.

(57) ABSTRACT

A magnetic sensor navigation system is disclosed, which includes: (a) a magnetic sensor array, including one or more magnetic non-Faradaic sensors; (b) a sensor interface operatively connected to receive a signal from each sensor of the array, wherein the sensor interface operates to generate a processed signal from one or more signals received from each sensor of the array; and (c) a processing and control unit connected to receive the processed signal, wherein the processing and control unit operates to calculate a spatial position of the sensor array using the processed signal when the sensor array is placed within a magnetic resonance environment of an MR scanner.

30 Claims, 5 Drawing Sheets

OTHER PUBLICATIONS

Kochli, V.D. et al, "Vascular Interventions guided by ultrafast MR imaging: evaluation of different materials", Magn Reson Med 1994; 31:309-314.

Bakker, C.J. et al, "Visualization of dedicated catheters using fast scanning techniques with potential for MR-guided vascular interventions", Magn Reson Med 1996; 36:816-820.

Dumoulin, C.L. et al, "Realtime position monitoring of invasive devices using MR", Magn Reson Med 1993; 29: 411-415.

Wildermuth, S. et al, "MR-guided percutaneous angioplasty: assessment of tracking safety, catheter handling and functionality", CVIR 1998; 21: 404-410.

Kee, S.T. et al, "MR-guided transjugular portosystemic shunt placement in a swine model", JVIR 1999; 10: 529-535.

Bernays, R.L. et al, "A new artifact-free device for frameless, magnetic resonance imaging-guided stereotactic procedures", Neurosurgery, Jan. 2000; 46(1):112-6.

Zhang, Q. et al, "A Multielement RF Coil for MRI Guidance of Interventional Devices", JMRI 2001; 14:56-62.

Ben-Haim, S.A. et al, "Nonfluoroscopic, in vivo navigation and mapping technology", Nat Med. Dec. 1996; 2(12):1393-5.

Kornowski, R. et al, "Preliminary animal and clinical experiences using an electromechanical endocardial mapping procedure to distinguish infarcted from healthy myocardium", Circulation, Sep. 15, 1998;98(11):1116-24.

Starkhammer, H. et al, "Central venous catheter placement using electromagnetic position sensing: a clinical evaluation", Biomedical Instrumentation and Technology 1996; 30: 164-170.

Shpun, S. et al, "Guidance of radiofrequency endocardial ablation with real-time three-dimensional magnetic navigation system", Circulation Sep. 16, 1997; 96(6):2016-21.

Tanase, D. et al, "Multi-parameter Sensor System with Intravascular Navigation for Catheter/Guide Wire Applications", Sensors and Actuators 2002; 97-98:116-124.

* cited by examiner

MAGNETIC FIELD SENSOR-BASED NAVIGATION SYSTEM TO TRACK MR IMAGE-GUIDED INTERVENTIONAL PROCEDURES

FIELD OF THE INVENTION

The present invention relates to a method and an apparatus for tracking and visualizing interventional devices during magnetic resonance imaging (MRI) scanning. More particularly, the present invention pertains to an active navigation technique and apparatus that utilizes direct measurement of local linear magnetic field gradients, which are used for image encoding in the MR environment, by using either Hall sensors or other magnetically sensitive sensing devices. In this way, the present invention provides information for tracking and visualizing an interventional device based on direct measurements of the local linear magnetic field gradients and not via the measurement of the nuclear magnetic resonance signal.

BACKGROUND OF THE INVENTION

As is generally known, magnetic resonance (MR) imaging has several unique attributes that can be exploited for guiding minimally invasive interventions. Among these include (a) an inherent high tissue contrast with the ability to manipulate contrast differences using various pulse sequences (or contrast agents), (b) a multi-planar imaging capability, and (c) the avoidance of ionizing radiation. In addition to detailed anatomic information, MRI technologies also provide useful physiological information on blood flow, tissue perfusion and diffusion (also referred to as "functional imaging"), and temperature changes in the imaged subject that can be used for monitoring responses to therapy and interventional techniques.

The poor visibility and tractability of interventional devices, such as puncture needles, guidewires, catheters, and the like, is a major problem encountered during MRI guided interventional procedures. While these interventional devices produce an excellent contrast in x-ray images, this is generally not the case during MR imaging. The high MR signal of surrounding tissue masks small interventional devices, making them nearly invisible in MR images.

Several methods have been proposed for tracking and visualizing interventional devices within the MRI environment. These methods for tracking and visualising interventional devices in the MR environment can be classified as either passive or active methods. In general, MR image contrast generated with passive visualisation methods has proven insufficient to determine the exact spatial position of an interventional device within three-dimensional space, especially when the interventional device is relatively small such as when the device is a needle or a catheter. Consequently, prior art passive methods are not acceptable for guiding the imaging plane with respect to an instrument's location, such as required for interventional device tracking and visualization during a medical or surgical interventional procedure (See for example, Bernstein et al., Magn. Reson. Med., vol. 39:pp. 300-308, 1998; Bakker et al., Magn. Reson. Med., vol. 36:pp. 816-820, 1996).

On the other hand, active determination of the spatial position of an interventional device has proven more promising, and active tracking and visualization techniques have already been applied in several interventional procedures for the purposes of tracking and navigating the interventional device. These prior art active tracking and visualizing methods use MR micro coils or optical navigation systems to provide the spatial coordinates of the interventional device in the MR environment; therefore, these active methods do not rely on vague susceptibility artifacts created by the device itself within the MR image, such as occurs during passive tracking and visualization procedures.

The principle of the prior art active methods, which use one or more MR micro coils, is based on the spatially dependent frequency encoding of an MR signal induced within the micro coil by means of linear magnetic field gradients (See for example, Dumoulin et al., Magn. Reson. Med., vol. 29:pp. 411-415, 1993; Wildermuth et al., CVIR, vol. 21:pp. 404-410, 1998; Kee et. al., JVIR, vol. 10:pp. 529-535, 1999). The MR micro coil detects the local resonant frequency of spins exposed to gradient fields, which is subsequently decoded to determine the position of the MR coil. The orientation of the interventional device in three-dimensional space is determined from the judicious placement of two or three independent MR coils attached to the interventional device.

However, active navigation based on MR micro coils has several drawbacks when used within the MR environment. First, these active techniques require several additional receiver amplifiers and channels for each MR micro coil. Furthermore, the MR imaging sequence used to visualize the surrounding tissue has to be interleaved with a dedicated projection sequence required to assess the position of the MR micro coils as described in U.S. Pat. No. 5,307,808 to Dumoulin et al., and in Zhang et al., JMRI, vol. 14:pp. 56-62, 2001. These requirements reduce flexibility in choosing image parameters and increase scan time, which are both disadvantageous limitations.

Optical navigation is an alternative to the use of MR micro coils for the purpose of actively tracking and visualizing an interventional device. Active device tracking using optical systems is based on the principle of optical triangulation, such as discussed in Bernays et al., Neurosurgery, vol. 46(1): pp. 112-116, 2000. Unfortunately, these optical systems can only be used on open MR systems that provide a free optical access path to the camera of the optical system. Furthermore, these optical techniques cannot be used to track guidewires, or other optically transparent instruments, placed within the patient's body.

In the art of medicine, techniques have been investigated and utilized for the purpose of catheter localization combined with x-ray supervision that use spatially varying external magnetic fields as a magnetic source of instrument localization. These magnetic navigation systems are, or have been, provided by different manufacturers such as CARTO EP Navigation, NOGA Navigation System, TELESTAR, NAVION, or Flock of Birds (See for example, Ben-haim et al., No. Med., vol. 2(12):pp. 1393-1395, 1996; Kornowski et al., Circulation, vol. 98(11):pp. 1116-1124, 1998; Starkhammer et al., Biomedical Instrumentation and Technology, vol. 30:pp. 164-170, 1996; Shpun et al., Circulation, vol. 96(6): pp. 2016-2021, 1997). Another magnetic navigation system has been described for guiding endovascular interventions under x-ray monitoring (See Tanase et al., Sensors and Actuators, vols. 97-98:pp. 116-124, 2002; and U.S. Pat. No. 6,427, 314 B1 to Acker). These research groups have demonstrated that Hall sensor-based navigation, within an external field of up to 0.4 mT, is feasible up to a positional accuracy of 2-3 mm. However, these prior art magnetic navigation systems cannot be used within a MR environment.

The present invention endeavors to provide a new navigation system based on the measurement of the local and spatially dependent magnetic field generated within the MR magnet bore, which takes advantage of measurements of the highly precise, spatially varying magnetic field. The proposed method relies on a direct measurement of the local magnetic field by means of magnetically sensitive devices, such as Hall devices and the like, thereby providing measurements of the local magnetic field for determining the position of the interventional device in a manner that is totally independent of the simultaneously applied MR imaging process.

Accordingly, a primary object of the present invention is to overcome the disadvantages of the prior art methods and apparatuses, both passive and active, for tracking and visualizing interventional devices within the MR environment.

Another object of the present invention is to provide a method and apparatus for tracking and visualizing an interventional device in an MR environment.

Another object of the present invention is to provide a method and apparatus for tracking and visualizing an interventional device in both open and closed MRI scanners.

Another object of the present invention is to provide a method and apparatus for tracking and visualizing an interventional device in an MR environment by directly measuring local linear magnetic field gradients, but not via measuring the magnetic resonance signal.

Another object of the present invention is to provide a method and apparatus for tracking and visualizing an interventional device in an MR environment, wherein the method and apparatus reliably track and provide visualization of large or small interventional devices without using MR coils and other magnetic sensing devices that operate using Faraday's Law.

SUMMARY OF THE INVENTION

The present invention provides an active navigation technique based on a direct measurement, but not via MR, of the local linear magnetic field gradients used for image encoding within the MRI environment by using Hall sensors, or other magnetically sensitive devices. The potential advantage of the Hall sensor approach, compared to using micro MR coils of the prior art, is that the present invention takes advantage of a measuring principle that is totally independent, and decoupled, from MR image generation.

In particular, in accordance with a first apparatus embodiment of the present invention, a magnetic sensor navigation system is provided that includes: (a) a magnetic sensor array, including one or more magnetic non-Faradaic sensors; (b) a sensor interface operatively connected to receive a signal from each sensor of the array, wherein the sensor interface operates to generate a processed signal from one or more signals received from each sensor of the array; and (c) a processing and control unit connected to receive the processed signal, wherein the processing and control unit operates to calculate a spatial position of the sensor array using the processed signal when the sensor array is placed within a magnetic resonance environment of an MR scanner.

In accordance with a second apparatus embodiment, the magnetic sensor navigation system of the first apparatus embodiment is further modified to include an interventional device, wherein the one or more magnetic non-Faradaic sensors are detachably attached to the interventional device. In accordance with a third apparatus embodiment, the magnetic sensor navigation system of the second apparatus embodiment is further modified to include an a base member, wherein the magnetic sensor array is fixed to the base member and the base member is detachably attached to the interventional device.

In accordance with a fourth apparatus embodiment, the magnetic sensor navigation system of the first apparatus embodiment is further modified to include an interventional device, wherein the magnetic sensor array is fixed to the interventional device.

In accordance with a fifth apparatus embodiment, the magnetic sensor navigation system of the second apparatus embodiment is modified so the one or more magnetic non-Faradaic sensors are selected from the group consisting of Hall sensors and magneto-optical sensors. In accordance with a sixth apparatus embodiment, the magnetic sensor navigation system of the fifth apparatus embodiment is modified so that the magnetic sensor array includes three Hall sensors arranged mutually orthogonal to each other. In accordance with a seventh apparatus embodiment, the magnetic sensor navigation system of the fifth apparatus embodiment is modified so that the magnetic sensor array includes a single three-axis Hall sensor.

In accordance with an eighth apparatus embodiment, the magnetic sensor navigation system of the fourth apparatus embodiment is modified so the one or more magnetic non-Faradaic sensors are selected from the group consisting of Hall sensors and magneto-optical sensors. In accordance with a ninth apparatus embodiment, the magnetic sensor navigation system of the eighth apparatus embodiment is modified so that the magnetic sensor array includes three Hall sensors arranged mutually orthogonal to each other. In accordance with a tenth apparatus embodiment, the magnetic sensor navigation system of the eighth apparatus embodiment is modified so that the magnetic sensor array includes a single three-axis Hall sensor.

In accordance with an eleventh apparatus embodiment, the magnetic sensor navigation system of the fifth apparatus embodiment is modified so the sensor interface is operatively connected to each sensor by a connector, the connector comprising a copper wire having a plurality of ferrite cores mounted thereon. In accordance with a twelfth apparatus embodiment, the magnetic sensor navigation system of the eleventh apparatus embodiment is modified so a ferrite core is mounted about every 4 cm along the wire. In accordance with an thirteenth apparatus embodiment, the magnetic sensor navigation system of the eighth apparatus embodiment is modified so the sensor interface is operatively connected to each sensor by a connector, the connector comprising a copper wire having a plurality of ferrite cores mounted thereon. In accordance with a fourteenth apparatus embodiment, the magnetic sensor navigation system of the thirteenth apparatus embodiment is modified so a ferrite core is mounted about every 4 cm along the wire.

In accordance with an fifteenth apparatus embodiment, the magnetic sensor navigation system of the fifth apparatus embodiment is modified so the interventional device is selected from the group consisting of a needle, a catheter, a guidewire, a trocar, an endoscope and a laparoscope. In accordance with a sixteenth apparatus embodiment, the magnetic sensor navigation system of the eighth apparatus embodiment is modified so the interventional device is selected from the group consisting of a needle, a catheter, a guidewire, a trocar, an endoscope and a laparoscope.

In accordance with a first method embodiment of the present invention, a method of guiding an interventional device in a magnetic resonance environment is provided that includes the steps of: (a) providing an interventional device and a magnetic sensor navigation system, wherein the navigation system comprises: (i) a magnetic sensor array, including one or more magnetic non-Faradaic sensors attached to the interventional device; (ii) a sensor interface operatively connected to receive a signal from each sensor of the array, wherein the sensor interface operates to generate a processed signal from one or more signals received from each sensor of the array; and (iii) a processing and control unit connected to receive the processed signal, wherein the processing and control unit operates to calculate a spatial position of the sensor array using the processed signal when the sensor array is placed within a magnetic resonance environment of an MR scanner; (b) placing the interventional device and magnetic sensor array within a magnetic resonance environment generated by an MR scanner; (c) generating a signal by using homogenous and gradient magnetic fields of the magnetic resonance environment to induce the signal from the one or more magnetic non-Faradaic sensors; and (d) calculating a position of the magnetic sensor array and the interventional device using the signal generated by the one or more magnetic non-Faradaic sensors.

In accordance with a second method embodiment, the method in accordance with the first method embodiment is further modified to include the step of: (e) guiding movement of the interventional device within the magnetic resonance environment using the calculated position of the interventional device. In accordance with a third method embodiment, the method in accordance with the second method embodiment is modified so that each magnetic non-Faradaic sensor is a Hall sensor and the induced signal is a Hall voltage, and the method further includes the step of: (f) generating a processed signal with the sensor interface in response to induced Hall voltage received from the Hall sensor.

In accordance with a fourth method embodiment, the method in accordance with the third method embodiment is modified so the processing and control unit receives the processed signal and, in response, calculates the position of the magnetic sensor array and the interventional device. In accordance with a fifth method embodiment, the method in accordance with the fourth method embodiment is modified so the magnetic sensor array consists of three mutually orthogonal sensors and the calculated position includes x, y and z coordinates. In accordance with a sixth method embodiment, the method in accordance with the fourth method embodiment is modified so the magnetic sensor array consists of a single three-axis Hall sensor and the calculated position includes x, y and z coordinates.

Further objects, features and advantages of the present invention will become apparent from the Detailed Description of the Illustrative Embodiments, which follows, when considered together with the attached drawings.

DETAILED DESCRIPTION OF THE ILLUSTRATIVE EMBODIMENTS

Figure 1:
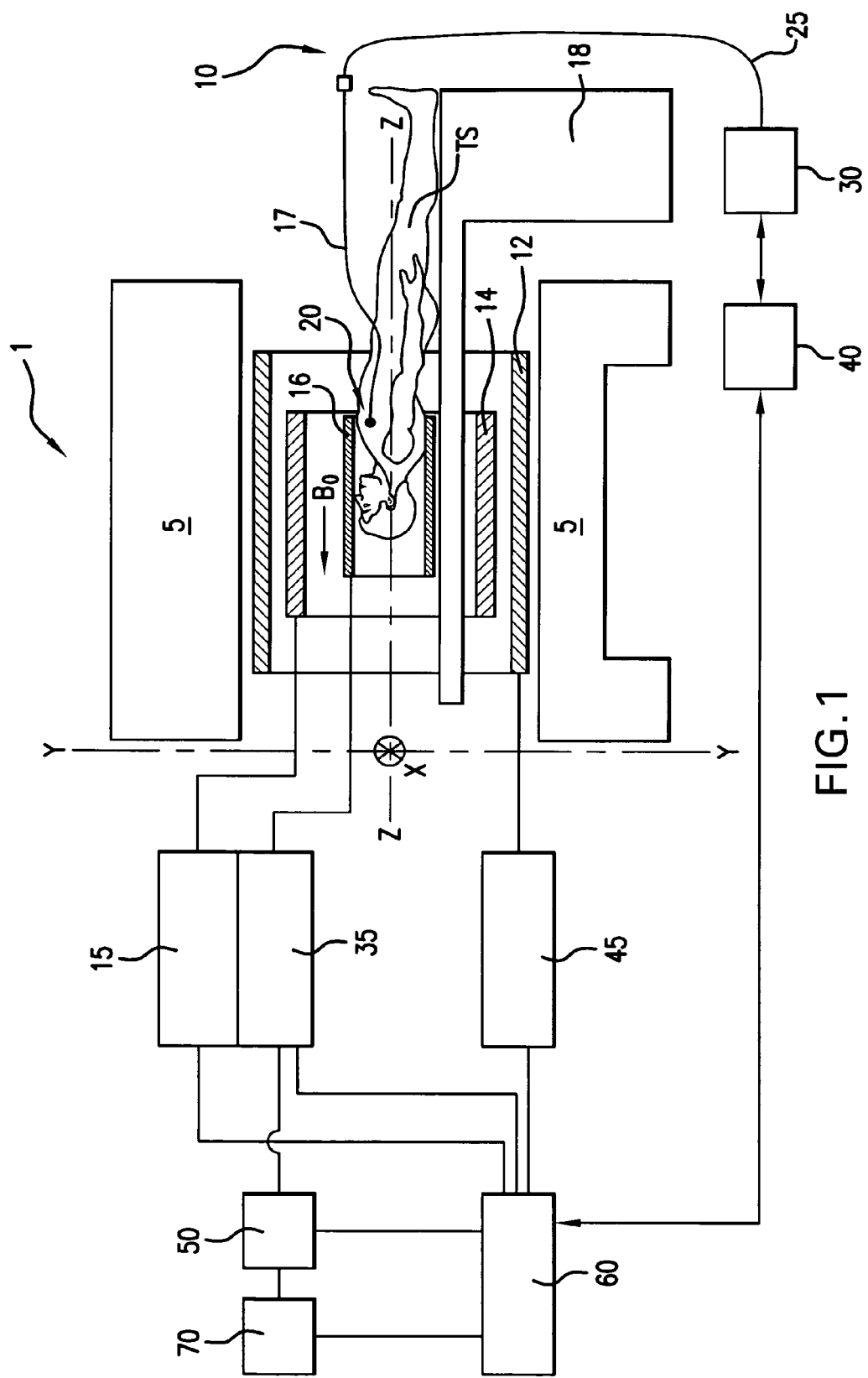
FIG. 1 schematically shows a magnetic sensor navigation system in accordance with the present invention, disposed within a conventional MR scanner.

The present invention includes both a method and apparatus for tracking and visualizing an interventional device in an MR environment. To facilitate an easy understanding of the present invention, the apparatus embodiment will be described first, with reference to the drawings. In the drawings, like parts are labeled with like reference numbers. Subsequently, a method embodiment for tracking and visualizing an interventional device in an MR environment will be described.

FIG. 1 illustrates the magnetic sensor navigation system 10 in accordance with the present invention, as it would be deployed in an MR environment, such as the interior of MRI scanner 1. In particular, FIG. 1 shows a test subject TS positioned along the z-axis of a conventional MRI scanner 1. Conventional MRI scanners and their imaging gradients are disclosed and described, for example, in U.S. Pat. No. 5,307,808 to Dumoulin et al. and in U.S. Pat. No. 6,516,213 B1 to Nevo, both of which are incorporated herein by reference. However, the magnetic sensor navigation system 10 of the present invention is not limited to use with any particular MRI scanner, but can be used generally with either open or closed MR scanners.

Generally, MRI scanner 1 has a magnet assembly that includes (a) magnet 5 for generating a uniform static magnetic field $B_0$ in the measuring space along the z-axis; (b) a gradient magnetic field coil assembly 12 for generating a gradient magnetic field in the measuring space; and (c) an RF coil 14 for generating an RF magnetic field in the measuring space. The magnet assembly of scanner 1 also includes an RF probe envelope (RF receiver coil) 16 positioned to detect MR signals generated by a test subject TS when the scanner is in use. A test subject positioning assembly 18 is generally provided for positioning and supporting the test subject TS during scanning.

Scanner 1 also includes an image processing assembly operably connected to the magnet assembly. The image processing assembly includes (a) a system control unit 60, (b) a gradient magnetic field power source 45, (c) an RF transmission unit 15, (d) a signal detection unit 35, (e) a signal processing unit 50, and (f) a display unit 70. The system control unit 60 is connected to send sequences of control pulses to the gradient magnetic field power source 45, which in turn is connected to send signals to the gradient magnetic field coil assembly 12. The gradient coil assembly 12 includes gradient magnetic field coils in the x, y and z directions, with each field coil generating gradient magnetic fields in accordance with signals received from the power source 45. In this way, a magnetic field gradient can be applied in a preselected direction to superimpose in the measuring space with the uniform static magnetic field generated by magnet 5 so that spins can be selectively excited and spatially encoded in a desired region (i.e., a slice or a slab) of the test subject TS.

The system control unit 60 is also connected to send control signals to the RF transmission unit 15, which is connected to send signals to RF coil 14 so that an RF magnetic field gradient is generated in the measuring space as well. The magnetic field gradient perturbs the selectively excited spins in the desired region, which then generate MR signals in the RF probe envelope 16 as they relax. The signal detection unit 35 is connected to the probe 16 and detects the MR signals induced in the probe. When MR signals are detected, the signal detection unit 35 sends detection signals to the signal processing unit 50, where they are processed and converted to image signals by calculation. The image signals are then displayed as an image on the display unit 70 and/or printed. The image signals can also be stored in a memory (not shown) of the system control unit 60.

The magnetic sensor navigation system 10, in accordance with the present invention, includes a magnetic sensor array 20 electrically connected via a wire or connector 25 so as to send electric signals to an electronic sensor interface 30. The sensor interface 30 processes the electronic signals received from the sensor array 20, and then sends the processed signals to a processing and control unit 40. The processing and control unit 40 then operates to calculate a spatial position of the sensor array using the processed signal, and sends output signals, corresponding to the calculated spatial position of the sensor array, as input to the control unit 60. The system control unit 60, which receives input signals from both the signal detection unit 35 and the processing and control unit 40, utilizes signal input from both the signal detection unit 35 and the processing and control unit 40 to generate the image signals that are then displayed as an image on the display unit 70 and/or printed, and/or stored in the memory of the system control unit 60.

Figure 2A:
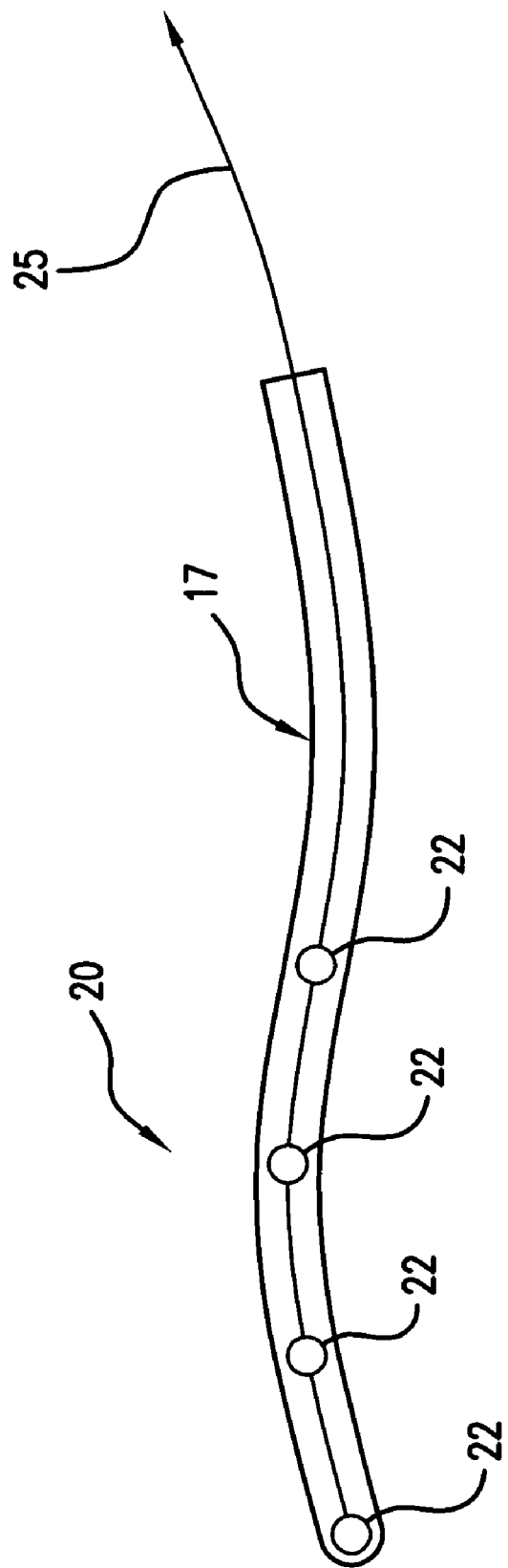
FIG. 2a schematically shows a first illustrative embodiment of the magnetic sensor array of the magnetic sensor navigation system in accordance with the present invention.
Figure 2B:
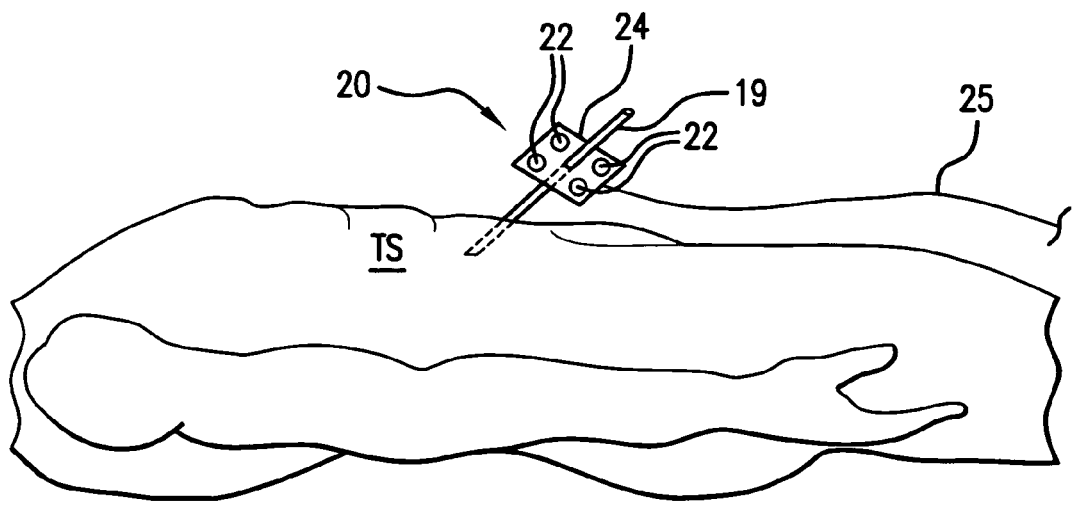
FIG. 2b schematically shows a second illustrative embodiment of the magnetic sensor array of the magnetic sensor navigation system in accordance with the present invention.

As shown in FIGS. 1, 2a and 2b, the magnetic sensor array 20 is attached to an interventional device, such as guidewire or catheter 17 or needle or needle holder 19, such as would be inserted into the test subject TS during a medical or surgical interventional procedure. For the purposes of this disclosure, an "interventional device" is any device used for medical and/or surgical procedures that can be used in an MR environment. A non-exclusive list of interventional devices usable in an MR environment includes needles, catheters, trocars, guidewires, endoscopes, laparoscopes, and like devices. In one embodiment in accordance with the present invention, the magnetic sensor array 20 is detachably attached to the interventional device, such as guidewire 17 or needle 19, while in other embodiments in accordance with the present invention the sensor array 20 is incorporated with the interventional device and is not feasibly detachable therefrom. In other words, the sensor array 20 is fixed to the interventional device in such embodiments so as to form a single unitary structure.

FIG. 2a schematically shows an illustrative guidewire or catheter embodiment in accordance with the present invention. Specifically, the magnetic sensor array 20 includes one or more magnetic sensors 22 that are mounted along, or mounted inside of, a guidewire or catheter 17. The one or more magnetic sensors 22 are electrically connected to send signals to the electronic sensor interface 30 via connector 25.

FIG. 2b schematically shows an illustrative needle or needle holder embodiment in accordance with the present invention. Specifically, the magnetic sensor array 20 includes one or more magnetic sensors 22 optionally disposed on, or mounted to, a base member 24. The base member 24 is constructed to attach to the interventional device, such as needle or needle holder 19, and may serve as a structure for facilitating the guidance and positioning of the interventional device. In a preferred embodiment, the magnetic sensor array 20 includes three magnetic sensors 22, each one corresponding to one of three orthogonal axis (i.e., x, y and z axis). Alternately, a three-axis magnetic sensing element (e.g., a three axis Hall sensor) could be used in place of the three orthogonal magnetic sensors 22. With the ability to sense or measure the local magnetic field in three dimensions, the magnetic sensor array 20 would provide signals corresponding to three dimensions needed to optimally localize an object in space. In this case, the object to be localized is the interventional device located within the imaging space of the MRI scanner 1.

Preferably, each magnetic sensor 22 is a Hall sensor, or other equivalent magnetically sensitive device, that can operate to directly measure a local magnetic field gradient. Magnetic sensors 22 in accordance with the present invention have the characteristic that they directly measure the local magnetic field in a way that is totally independent and decoupled from generation of the MR image. In view of this definition, MR micro coils are not magnetically sensitive devices equivalent to Hall sensors because MR micro coils (i.e. rf coils or Helmholtz coils) operate in accordance with Faraday's Law, which induces voltages by a set of time-varying electromagnetic gradient fields in the set of coils. Thus, MR micro coils are coupled to, and not independent of, MR image generation.

On the other hand, Hall sensors operate using the Hall effect where homogenous and gradient magnetic fields induce voltages in a set of miniature conductors carrying electrical current. Practically speaking, Hall sensors generate a Hall voltage that is proportional to the local magnetic field applied perpendicular to the Hall plate. The two main sources of magnetic fields generated within the imaging space of the MR scanner are (i) a very strong and static (i.e., homogenous) magnetic field $B_o$ of about 1.5 T to 3 T, and (ii) the additional field gradients along the x, y, and z directions. As is generally known, the magnetic field gradients are used for spatial encoding of the MR imaging process. These gradient fields generate a magnetic field that linearly depends on the spatial position along a certain principal axis. However, the strength of these magnetic field gradients is about 2 mT at a 10 cm off-center position (i.e., off the z-axis). In other words, the magnetic field gradients are much smaller in magnitude than the 1.5 T main magnetic field $B_o$. Because there is a linear dependence of the local magnetic field in the image space of the MR scanner on spatial position in the presence of magnetic field gradients, the measured Hall voltage produced within each sensor 22 can be used to determine its spatial position.

In alternate embodiments, such as when the interventional device is a guidewire 17, the Hall sensors can be mounted, for example, on the tip of the guidewire or at several positions along the guidewire. In another alternate embodiment, the base member 24 is a guidance device, such as are known in the art, and the Hall sensors are attached on the guidance device to guide the interventional device in puncture or stereotactic procedures. FIG. 1 shows an embodiment wherein the interventional device is a guidewire or catheter 17, such as shown in FIG. 2a, which is threaded through a blood vessel of the test subject TS. On the other hand, FIG. 2b shows an embodiment wherein the base member 24 is a guidance device and the sensors 22 are attached on the guidance device. In this illustration, the interventional device is a needle 19 and the needle position can be calculated, by the system control unit 60, from the measured orientation, (i.e. the Hall effect signals provided by one or more sensors 22), of the guidance device.

In other words, signals from the sensors 22 are processed by the processing and control unit 40, which in turn sends calculated position signals to the system control unit 60. The system control unit 60 then uses these signals received from processing and control unit 40, and signals received from signal detection unit 35, to generate combined image signals. The combined image signals are then displayed as a combined image on the display unit 70 and/or printed, and/or stored in the memory of the system control unit 60. The combined image is the scanned MR image with a corresponding image of the interventional device incorporated with, or projected onto, the scanned MR image so as to make the interventional device visable in the combined image. The image of the interventional device is calculated based upon the positional/spatial sensor data collected from the sensors 22.

Measurement of Spatial Position

The magnetic field within the usable space of the MR scanner 1 (i.e., the imaging space) is composed of a static magnetic field $B_0=(0,0,B_0)$, and additionally three independent linear magnetic field gradients (Gx,Gy,Gz) oriented respectively along the principal axis x, y, and z. The resulting, local magnetic field then is represented by [x1]

$$\vec{B}(\vec{r}) - \vec{B}_0 = \begin{pmatrix} -\frac{1}{2}G_z & 0 & G_x \\ 0 & \frac{1}{2}G_z & G_y \\ G_x & G_y & G_z \end{pmatrix} \begin{pmatrix} x \\ y \\ z \end{pmatrix}.$$

A three-axis Hall element, or alternatively three single-axis Hall elements arranged mutually orthogonal to each other, provides a sensor that generates three independent Hall voltages $U_H(r)$. $U_H(r)$ is a function that depends on the following parameters: (i) local field B(r), (ii) on the sensitivity of the Hall elements (s1,s2,s3), and (iii) on the orientation ($\phi$, $\theta$) of the Hall sensors (r=(x,y,z)). The Hall voltages that are produced by the static $B_o$ field alone can be subtracted from $U_H$ (for example, by subtracting two measurements acquired during opposite gradient polarities), resulting in:

$$\vec{U}_H(\vec{r}) = \begin{pmatrix} s_1 & 0 & 0 \\ 0 & s_2 & 0 \\ 0 & 0 & s_3 \end{pmatrix} \begin{pmatrix} \sin\theta\cos\varphi & \cos\theta\cos\varphi & \sin\varphi \\ \sin\theta\sin\varphi & \cos\theta\sin\varphi & -\cos\varphi \\ \cos\theta & -\sin\theta & 0 \end{pmatrix} \begin{pmatrix} -\frac{1}{2}G_z & 0 & G_x \\ 0 & \frac{1}{2}G_z & G_y \\ G_x & G_y & G_z \end{pmatrix} \begin{pmatrix} x \\ y \\ z \end{pmatrix}$$

The five unknown variables ($\phi$, $\theta$, x, y, z) can be determined, for example, from three independent measurements, which provide 9 measured Hall voltages. From these nine measured Hall voltages, the spatial coordinates (x, y, z) of the sensor as well its orientation ($\phi$, $\theta$) can be calculated.

Advantages of the apparatus and method embodiments in accordance with the present invention, when compared to existing prior art apparatuses and methods, include:

1) The spatial localization of the sensor can be measured simultaneously during the run of any arbitrary MR imaging sequence because imaging sequences, in general, use all three gradient axes.
2) The method of measuring the local magnetic field, in accordance with the present invention, does not interfere with the MR imaging process because magnetic fields are directly measured rather than measuring an MR signal.
3) A higher positional accuracy is expected than the accuracy achieved by the existing methods of the prior art.
4) The Hall sensors are very small in size (about 100 µm×100 µm×100 µm), which is much smaller than rf coils and other devices used in the prior art.
5) Very tiny copper wires (e.g., wires having a radius of 10 µm) can be attached to the sensors 22, which is not possible when constructing the prior art apparatuses or practicing the prior art methods.

In view of the present disclosure, those skilled in the art would realize that the present invention utilizes the magnetic field gradients generated by the MRI system to provide spatial information, which is used to track, visualize and guide an interventional device within the MR imaging space. Thus, the present invention efficiently combines MR imaging with navigation by using the magnetic gradient fields required for imaging as the source for spatial information for magnetic field sensor-based navigation. This feature of the present invention distinguishes it from apparatuses for magnetic determination of position and orientation, such as disclosed in U.S. Pat. No. 5,558,091 (Acker et al.) and U.S. Pat. No. 6,427,314 B1 (Acker), both of which utilize external Helmholtz coils for providing the spatially dependent magnetic gradient fields. Likewise, the present invention is distinguished from the device disclosed in U.S. Pat. No. 5,307,808 (Dumoulin et al.), which utilizes an rf coil (i.e., a Faradaic device) to generate detection signals having Larmor frequencies, and the device disclosed in U.S. Pat. No. 6,516,213 B1 (Nevo), which utilizes multiple orthogonal sensing coils (i.e. a Faradaic device) to detect the time-derivative of the magnetic field by induction rather than directly measuring the magnetic field itself.

EXAMPLE 1

Figure 3:
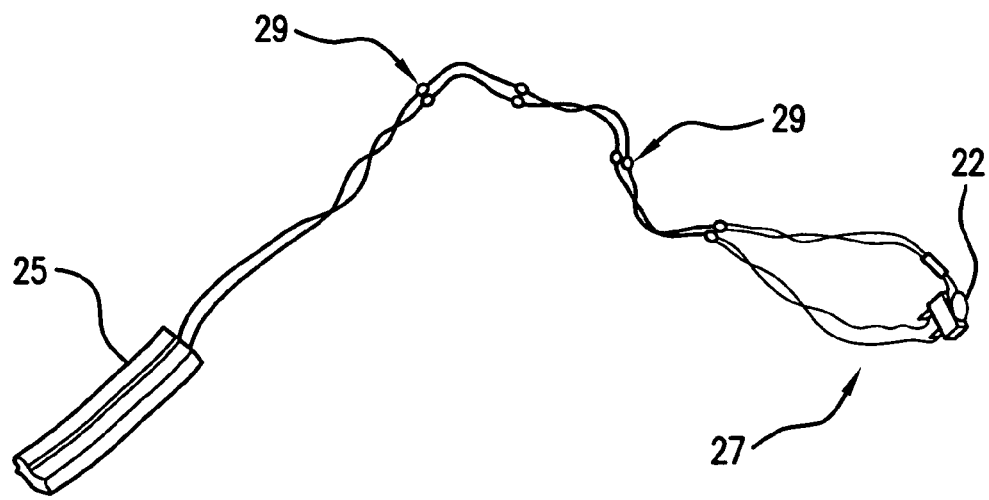
FIG. 3 shows a single Hall sensor device, such as is used in an illustrative embodiment, in accordance with the present invention.

The present example demonstrates the effective measurement of local magnetic fields within the MR scanner by means of Hall sensors using a very simple Hall sensor array as shown in FIG. 3. A commercially available Hall sensor device 22 (HW-105C, sensitivity 2V/T at 15 mA Hall current, AKE, Tokyo, Japan) with a single sensitivity direction was connected to four pairwise twisted copper wires 27 (PU insulated, 100 µm), as shown in FIG. 3. The dimensions of this Hall sensor are 1.5×1×0.5 mm$^3$. In order to reduce the induction of RF energy in the copper wires 27, small ferrite cores 29 have been mounted every 4 cm along the wire.

Figure 4A:
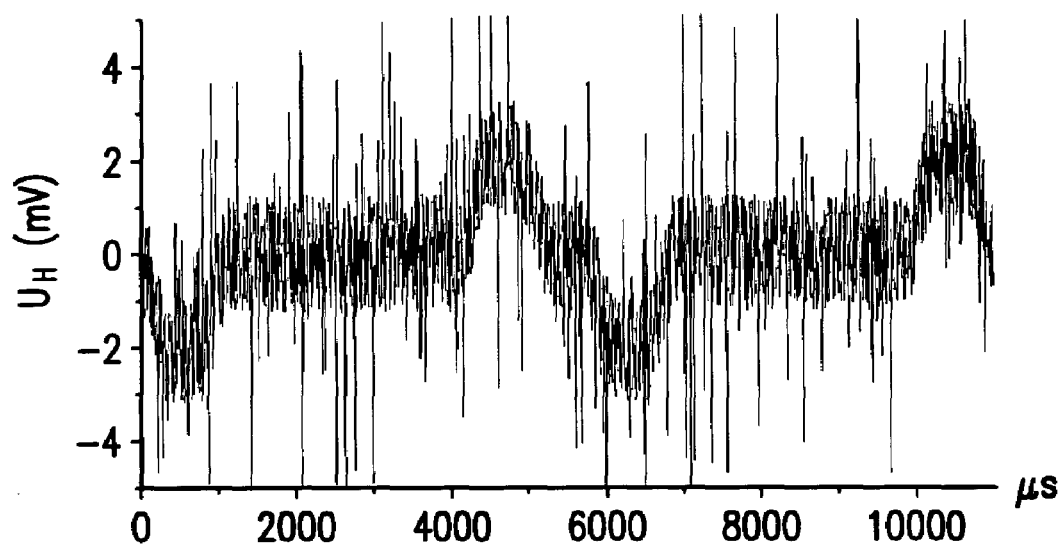
FIG. 4 provides three graphs of measured Hall voltage as follows: Graph (A), Measured Hall voltage without averaging; Graph (B), Measured Hall voltage with averaging; and Graph (C), measured and averaged Hall voltage graphed as a function of z-position.
Figure 4B:
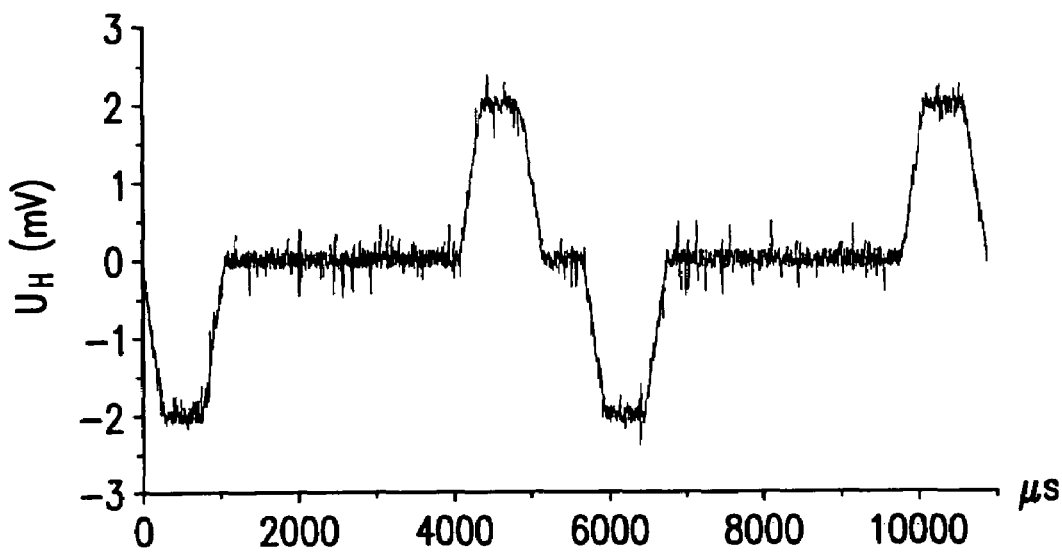
Figure 4C:
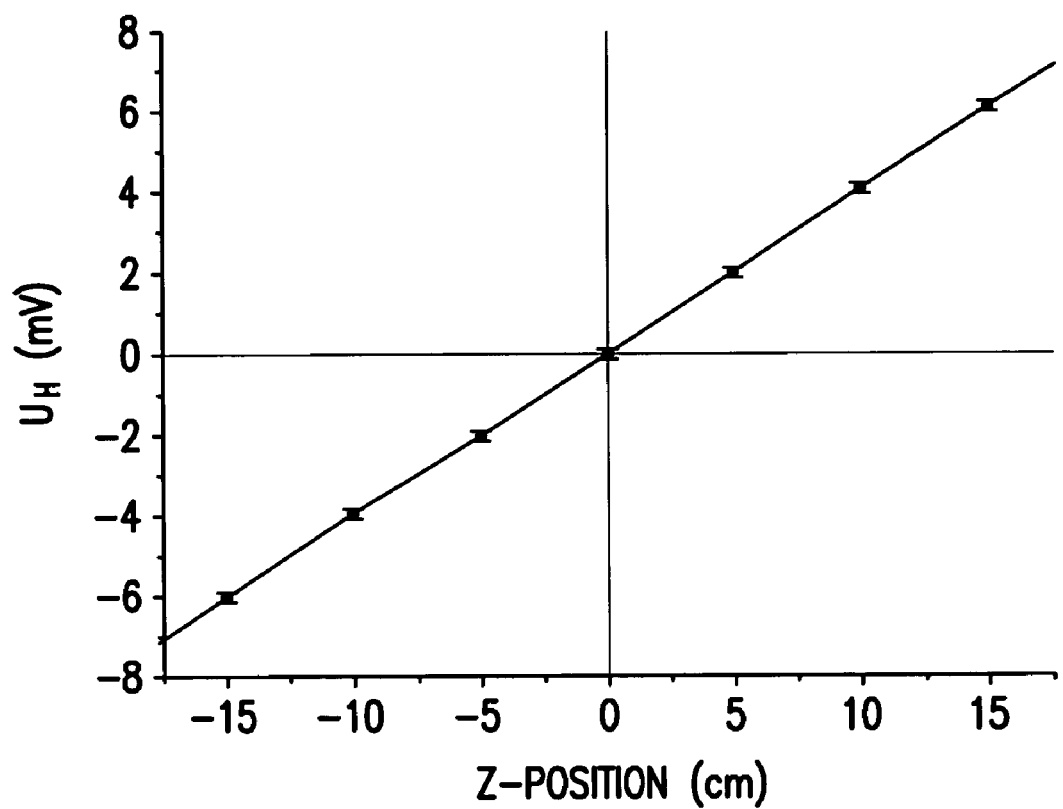

The Hall voltage was amplified with an ac-coupled instrumental amplifier, followed by a 16-Bit ADC (PCI-6014, National Instruments). Hall voltage was measured at different spatial positions and orientations within the MR scanner imaging space during the run of constant, bipolar magnetic field gradient pairs, as well as during a balanced steady state free precession (TrueFISP) imaging sequence. Graph A in FIG. 4 shows the Hall voltage (5 µs sampling rate) generated by a switched phase encoding gradient in z-direction (ramp 300 µs, flat top 500 µs at 20 mT/m). The sensor 22 was positioned +5 cm off-center. The change of the Hall voltage was ±2 mV with a noise component of about 1.0 mV$_{eff}$.

The noise induced by the sensor and amplifier translates into an error of the spatial position of roughly ±2.5 cm at 20 mT/m. However, by averaging several phase encoding cycles the spatial accuracy is readily improved to less than ±2 mm. For example, assuming a repetition time of the switched gradients of 5.2 ms, as evident from graph A of FIG. 4, an averaging of 128 phase encoding steps (as typically used for real-time imaging) results in an increase in spatial accuracy by a factor of 11 while the temporal resolution is maintained at about 0.7 sec (128×5.2 ms). Graph B of FIG. 4 shows the averaged time course for a constant phase encoding amplitude during 128 encoding steps. Graph C of FIG. 4 shows the measured sensor position as a function of the z-position. Indicated error bars correspond to ±0.1 mV or ±2 mm at 20 mT/m.

Thus, the data complied in the three graphs of FIG. 4 demonstrate the ability to use a Hall sensor to detect the spatial position of the Hall sensor with an accuracy of about 2 mm during the run of an MR imaging sequence. One potential problem when using conducting wires in an MR environment is electric coupling with the transmitted RF field, which may lead to severe heating in the wires. However, the mounting of small ferrite cores along the wire as used in Example 1, or by using optical signal transmission along optical micro fibres, such undesirable heating effects can be reduced.

EXAMPLE 2

In Example 2, the Hall sensor described in Example 1 is utilized to construct a magnetic sensor navigation system in accordance with the present invention. In this illustrative embodiment, the magnetic sensor array consists of a single Hall sensor (HW-105C, sensitivity 2V/T at 15 mA Hall current, AKE, Tokyo, Japan) with a single sensitivity direction. This Hall sensor, with a single sensitivity direction, is connected to four, pairwise twisted copper wires (PU insulated, 100 μm), which are themselves electrically connected via a larger wire or connector so as to be able to send electric signals to a sensor interface. The sensor interface operates to process electronic signals received from the Hall sensor, and then sends the processed signals to a processing and control unit that operates to calculate the position of the sensor from induced Hall voltages. In addition, an ac-coupled instrumental amplifier followed by a 16-Bit ADC (PCI-6014, National Instruments) are connected between the Hall sensor and the sensor interface, or are alternatively incorporated with the sensor interface, in order to amplify the Hall voltage signals.

The Hall sensor is preferably incorporated in an interventional device, such as an endoscope or laparoscope. Alternatively, the Hall sensor is incorporated into the distal end of a cardiac catheter or other suitable intravenous catheter.

As noted above, magnetic sensors used in constructing a magnetic sensor navigation system, in accordance with the present invention, do not operate under Faraday's principle; therefore, the class of magnetic sensors used in the present invention can be referred to as "non-Faradaic magnetic sensors." The Hall sensor described above, which operates under the principle of the Hall effect, is one example of a non-Faradaic magnetic sensor. Another example of non-Faradaic magnetic sensors suitable for use in the present invention are magneto-optical sensors, such as disclosed in U.S. Pat. No. 6,111,416 to Zhang et al., which is incorporated herein by reference.

Method Embodiment

Having fully and completely described various apparatus embodiments in accordance with the present invention, an illustrative method embodiment for tracking and visualizing an interventional device in an MR environment will be outlined below. More particularly, an illustrative method in accordance with the present invention is a method of guiding an interventional device in a magnetic resonance environment, which includes the steps of: (a) providing a magnetic sensor navigation system in accordance with the present invention, such as a system comprising: (i) a magnetic sensor array, including one or more magnetic non-Faradaic sensors attached to an interventional device; (ii) a sensor interface operatively connected to receive a signal from each sensor of the array, wherein the sensor interface operates to generate a processed signal from one or more signals received from each sensor of the array; and (iii) a processing and control unit connected to receive the processed signal, wherein the processing and control unit operates to calculate a spatial position of the sensor array using the processed signal when the sensor array is placed within a magnetic resonance environment of an MR scanner; (b) placing the interventional device with the magnetic sensor array within a magnetic resonance environment generated by an MR scanner; (c) generating a signal by using homogenous and gradient magnetic fields of the magnetic resonance environment to induce the signal from the one or more magnetic non-Faradaic sensors; (d) using the sensor interface to receive the signal and, in response, to generate a processed signal; (e) using the processing and control unit to receive the processed signal and to calculate a position of the magnetic sensor array and the interventional device; and (f) using the calculated position of the interventional device to guide movement of the interventional device within the magnetic resonance environment.

The method in accordance with the present invention can be practiced using any suitable magnetic non-Faradaic sensors, such as Hall sensors or magneto-optical sensors. In one illustrative embodiment, the sensors are Hall sensors so the induced signal is a Hall voltage. When the magnetic sensor arrays consists of either three mutually orthogonal Hall sensors, or a single three-axis Hall sensor, then the calculated position includes x, y and z coordinates for the sensor array and the interventional device, and the orientation ($\phi$, $\theta$) of the sensor array and the interventional device (r=(x,y,z)) can be calculated as well.

While the present invention has been described with reference to certain illustrative embodiments, one of ordinary skill in the art will recognize that additions, deletions, substitutions, modifications and improvements can be made while remaining within the scope and spirit of the present invention as defined by the appended claims.

What is claimed is:

1. A magnetic sensor navigation system comprising:
   (a) a magnetic sensor array, including one or more magnetic non-Faradaic sensors;
   (b) a sensor interface operatively connected to receive a first signal from each sensor of the array, wherein the sensor interface operates to generate a processed signal from one or more first signals received from each sensor of the array;
   (c) an MR scanner having a magnetic resonance environment; and
   (d) processing and control unit connected to receive the processed signal, wherein the processing and control unit operates to calculate a spatial position of the sensor array using the processed signal when the sensor array is placed within the magnetic resonance environment of the MR scanner, wherein the MR scanner comprises
      i. a magnet generating a first homogenous static magnetic field along a z-axis of a measuring space of the MR scanner;
      ii. a gradient magnetic field coil assembly for generating a second gradient magnetic field in the measuring space, wherein the gradient magnetic field coil assembly includes three gradient magnetic field coils disposed so as to be linearly independent of one another; and
      iii. an RF coil for generating a third RF magnetic field in the measuring space,
   wherein the magnetic resonance environment comprises the first homogenous static magnetic field generated by the magnet of the MR scanner and the second gradient magnetic field generated by the gradient magnetic field coil assembly of the MR scanner and the third RF magnetic field generated by the RF coil of the MR scanner, and wherein the one or more magnetic non-Faradaic sensors use the first homogenous magnetic field and the second gradient magnetic field of the magnetic resonance environment to generate the one or more first signals.

2. A magnetic sensor navigation system as recited in claim 1, further comprising an interventional device, wherein the one or more magnetic non-Faradaic sensors are detachably attached to the interventional device.

3. A magnetic sensor navigation system as recited in claim 2, further comprising a base member, wherein the magnetic sensor array is fixed to the base member and the base member is detachably attached to the interventional device.

4. A magnetic sensor navigation system as recited in claim 2, wherein the one or more magnetic non-Faradaic sensors are selected from the group consisting of Hall sensors and magneto-optical sensors.

5. A magnetic sensor navigation system as recited in claim 4, wherein the magnetic sensor array comprises three Hall sensors arranged mutually orthogonal to each other.

6. A magnetic sensor navigation system as recited in claim 4, wherein the magnetic sensor array comprises a single three-axis Hall sensor.

7. A magnetic sensor navigation system as recited in claim 4, wherein the magnetic sensor array consists of three Hall sensors arranged mutually orthogonal to each other.

8. A magnetic sensor navigation system as recited in claim 4, wherein the magnetic sensor array consists of a single three-axis Hall sensor.

9. A magnetic sensor navigation system as recited in claim 4, wherein the sensor interface is operatively connected to each sensor by a connector, the connector comprising a copper wire having a plurality of ferrite cores mounted thereon.

10. A magnetic sensor navigation system as recited in claim 9, wherein a ferrite core is mounted about every 4 cm along the wire.

11. A magnetic sensor navigation system as recited in claim 4, wherein the interventional device is selected from the group consisting of a needle, a catheter, a guidewire, a trocar, an endoscope and a laparoscope.

12. A magnetic sensor navigation system as recited in claim 1, further comprising an interventional device, wherein the magnetic sensor array is fixed to the interventional device.

13. A magnetic sensor navigation system as recited in claim 12, wherein the one or more magnetic non-Faradaic sensors are selected from the group consisting of Hall sensors and magneto-optical sensors.

14. A magnetic sensor navigation system as recited in claim 13, wherein the magnetic sensor array comprises three Hall sensors arranged mutually orthogonal to each other.

15. A magnetic sensor navigation system as recited in claim 13, wherein the magnetic sensor array comprises of a single three-axis Hall sensor.

16. A magnetic sensor navigation system as recited in claim 13, wherein the magnetic sensor array consists of three Hall sensors arranged mutually orthogonal to each other.

17. A magnetic sensor navigation system as recited in claim 13, wherein the magnetic sensor array consists of a single three-axis Hall sensor.

18. A magnetic sensor navigation system as recited in claim 13, wherein the sensor interface is operatively connected to each sensor by a connector, the connector comprising a copper wire having a plurality of ferrite cores mounted thereon.

19. A magnetic sensor navigation system as recited in claim 18, wherein a ferrite core is mounted about every 4 cm along the wire.

20. A magnetic sensor navigation system as recited in claim 13, wherein the interventional device is selected from the group consisting of a needle, a catheter, a guidewire, a trocar, an endoscope and a laparoscope.

21. A magnetic sensor navigation system as recited in claim 1, wherein the system does not include any additional MR coils for generating the one or more first signals.

22. A magnetic sensor navigation system as recited in claim 1, wherein the three gradient magnetic field coils are orthogonally disposed to one another.

23. A method of guiding an interventional device in a magnetic resonance environment, the method comprising the steps of:
(a) providing an interventional device and a magnetic sensor navigation system, wherein the navigation system comprises:
    i. a magnetic sensor array, including one or more magnetic non-Faradaic sensors attached to the interventional device;
    ii. a sensor interface operatively connected to receive a first signal from each sensor of the array, wherein the sensor interface operates to generate a processed signal from one or more first signals received from each sensor of the array; and
    iii. a processing and control unit connected to receive the processed signal, wherein the processing and control unit operates to calculate a spatial position of the sensor array using the processed signal when the sensor array is placed within a magnetic resonance environment of an MR scanner;
(b) placing the interventional device and magnetic sensor array within the magnetic resonance environment generated by an MR scanner, wherein the MR scanner comprises
    i. a magnet generating a first homogenous static magnetic field along a z-axis of a measuring space of the MR scanner;
    ii. a gradient magnetic field coil assembly for generating a second gradient magnetic field in the measuring space, wherein the gradient magnetic field coil assembly includes three gradient magnetic field coils disposed so as to be linearly independent of one another; and
    iii. an RF coil for generating a third RE magnetic field in the measuring space so that the magnetic resonance environment comprises the first homogenous static magnetic field generated by the magnet and the second gradient magnetic field generated by the gradient magnetic field coil assembly and the third RF magnetic field generated by the RF coil;
(c) generating the one or more first signals by using the first homogenous magnetic field and the second gradient magnetic field of the magnetic resonance environment to induce the one or more first signals from the one or more magnetic non-Faradaic sensors; and
(d) calculating a position of the magnetic sensor array and the interventional device using the one or more first signals generated by the one or more magnetic non-Faradaic sensors.

24. A method as recited in claim 23, further comprising the step of:
(e) guiding movement of the interventional device within the magnetic resonance environment using the calculated position of the interventional device.

25. A method as recited in claim 24, wherein each magnetic non-Faradaic sensor is a Hall sensor and the induced first signal is a Hall voltage, and the method further comprises the step of:
(f) generating a processed signal with the sensor interface in response to induced Hall voltage received from the Hall sensor.

26. A method as recited in claim 25, wherein the processing and control unit receives the processed signal and, in response, calculates the position of the magnetic sensor array and the interventional device.

27. A method as recited in claim 26, wherein the magnetic sensor array consists of three mutually orthogonal sensors and the calculated position includes x, y and z coordinates.

28. A method as recited in claim 26, wherein the magnetic sensor array consists of a single three-axis Hall sensor and the calculated position includes x, y and z coordinates.

29. A. method as recited in claim 23, wherein the method does not employ any additional MR coils in order to generate the one or more first signals.

30. A method as recited in claim 23, wherein the three gradient magnetic field coils are orthogonally disposed to one another.

* * * * *